(12) United States Patent  (10) Patent No.: US 8,701,463 B2
Brasfield  (45) Date of Patent: *Apr. 22, 2014

(54) TARGET ODOR DETECTION AND SECURITY APPARATUS

(76) Inventor: Freddie R. Brasfield, Oak Ridge, TN (US)

( * ) Notice: Subject to any disclaimer, the term of this patent is extended or adjusted under 35 U.S.C. 154(b) by 420 days.

This patent is subject to a terminal disclaimer.

(21) Appl. No.: 13/160,075

(22) Filed: Jun. 14, 2011

(65) Prior Publication Data

US 2012/0151993 A1  Jun. 21, 2012

Related U.S. Application Data

(63) Continuation-in-part of application No. 13/029,839, filed on Feb. 17, 2011, which is a continuation-in-part of application No. 11/859,851, filed on Sep. 24, 2007, now Pat. No. 7,913,540.

(51) Int. Cl.
*G01N 33/497* (2006.01)

(52) U.S. Cl.
USPC .......................................... 73/23.34

(58) Field of Classification Search
USPC ................ 73/23.34, 23.2, 23.42, 864.33
See application file for complete search history.

(56) References Cited

U.S. PATENT DOCUMENTS

| | | |
|---|---|---|
| 3,357,257 A | 12/1967 | Herndon et al. |
| 3,883,739 A | 5/1975 | Jenkins |
| 4,022,054 A | 5/1977 | Biederman |
| 4,202,200 A | 5/1980 | Ellson |
| 4,411,156 A | 10/1983 | Lowe |
| 4,896,547 A | 1/1990 | Arney et al. |
| 4,987,767 A | 1/1991 | Corrigan et al. |
| 5,109,691 A | 5/1992 | Corrigan et al. |
| 5,600,303 A | 2/1997 | Husseiny et al. |
| 5,753,832 A | 5/1998 | Bromberg et al. |
| 5,915,268 A | 6/1999 | Linker et al. |
| 6,018,984 A | 2/2000 | McGinley et al. |
| 6,073,499 A | 6/2000 | Settles |
| 6,295,860 B1 | 10/2001 | Sakairi et al. |
| 6,334,365 B1 | 1/2002 | Linker et al. |
| 6,366,203 B1 | 4/2002 | Burns |
| 6,374,662 B1 | 4/2002 | Oda et al. |
| 6,375,697 B2 | 4/2002 | Davies |
| 6,558,626 B1 | 5/2003 | Aker et al. |
| 6,610,977 B2 | 8/2003 | Megerle |
| 6,708,572 B2 | 3/2004 | Jenkins et al. |
| 6,782,845 B1 | 8/2004 | Schmidt et al. |
| 6,790,249 B2 | 9/2004 | Davies |
| 6,823,714 B2 | 11/2004 | Megerle |
| 6,919,202 B2 | 7/2005 | Lewis et al. |
| 6,972,693 B2 | 12/2005 | Brown et al. |
| 7,023,339 B2 | 4/2006 | Stomski |
| 7,091,856 B2 | 8/2006 | Tibi et al. |

(Continued)

FOREIGN PATENT DOCUMENTS

| | | |
|---|---|---|
| WO | 0229744 | 4/2002 |
| WO | 2004085251 | 10/2004 |

*Primary Examiner* — John Fitzgerald
(74) *Attorney, Agent, or Firm* — Robinson IP Law, PLLC

(57) ABSTRACT

A target odor detection apparatus and system configured to house one or more inanimate odor detectors for screening air passed across odor emitters or conveyances that pass through the target odor detection apparatus. Various communication technologies are incorporated in certain embodiments to provide enhanced control over an apparatus or system located in multiple and, in some cases, very distant, geographic locations.

20 Claims, 11 Drawing Sheets

(56) References Cited

U.S. PATENT DOCUMENTS

| | | |
|---|---|---|
| 7,141,786 B2 | 11/2006 | McGann et al. |
| 7,180,441 B2 | 2/2007 | Rowe et al. |
| 7,357,043 B2 | 4/2008 | Cumming et al. |
| 7,717,066 B2 * | 5/2010 | Drolet ........................ 119/421 |
| 7,913,540 B2 * | 3/2011 | Brasfield ..................... 73/23.34 |
| 2001/0049926 A1 * | 12/2001 | Davies ........................ 55/385.2 |
| 2003/0085348 A1 * | 5/2003 | Megerle ...................... 250/287 |
| 2004/0232054 A1 * | 11/2004 | Brown et al. ................. 209/552 |
| 2006/0150872 A1 | 7/2006 | Mesinger |
| 2007/0056392 A1 * | 3/2007 | Cumming et al. ......... 73/864.33 |
| 2009/0038555 A1 | 2/2009 | Reese |
| 2009/0077908 A1 * | 3/2009 | Brasfield ........................ 52/198 |
| 2009/0139459 A1 | 6/2009 | Habacivch et al. |
| 2009/0162196 A1 | 6/2009 | Drolet |
| 2010/0180667 A1 | 7/2010 | Bender et al. |
| 2012/0103060 A1 * | 5/2012 | Brasfield ..................... 73/23.34 |
| 2012/0151993 A1 * | 6/2012 | Brasfield ..................... 73/23.34 |

* cited by examiner

TARGET ODOR DETECTION AND SECURITY APPARATUS

CROSS-REFERENCE(S) TO RELATED APPLICATION(S)

This application claims priority to now pending U.S. application Ser. No. 13/029,839 to Freddie R. Brasfield entitled "Target Odor Detection and Security Apparatus" which was originally filed on Feb. 17, 2011, which claims priority to U.S. application Ser. No. 11/859,851 (now U.S. Pat. No. 7,913, 540) to Freddie R. Brasfield entitled "Odor Screening System," the content of which are incorporated herein by reference in their respective entireties.

FIELD

This disclosure relates to the field of odor screening for distinctive odors emitted by prohibited materials. More particularly, this disclosure relates to a method and apparatus for collecting odor samples from conveyances and supplying the odor samples to an inanimate odor detector for identification of target odors of prohibited materials.

BACKGROUND

There are many situations in which packages, pedestrians, vehicles and the like (conveyance) may be carrying materials which are prohibited from transport into or out of a designated area. Some examples are airports, sporting arenas and high security facilities. The prohibited materials may include, for example, explosives, drugs or even a product being stolen.

One method for screening for various materials is to individually search each conveyance for the prohibited material. Unfortunately, individual searching is extremely time-consuming and requires an inordinate number of searchers and an inordinate period of time.

It is known that many prohibited materials such as explosives and drugs emit odors which are distinctive and can be detected in very small quantities by specialized inanimate detectors which have been calibrated to identify such target odors. However, bringing expensive and often cumbersome detection equipment into direct contact with a large number of pedestrians and/or vehicles presents risks. Discrete placement of such equipment is important as well as the protection of the equipment itself, which is often expensive, and protection of personnel responsible for such equipment.

What is needed, therefore, is a reliable and consistent system to screen persons or conveyances and obtain consistent positive identifications of prohibited material while achieving, for example, some or all of the goals listed above.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Air: broadly defined to include a scientific definition of "air" and/or other pure gases and gas mixtures and all solid, liquid, and gaseous substances entrained therein.

Airflow inducer: an apparatus used to cause air to move relative to the apparatus (e.g., a fan, a pump, or other similar device, with or without moving mechanical parts) by pushing or pulling such air.

Inanimate Odor Detector: A non-living device that has been calibrated or otherwise has learned through, for example, computer-based learning algorithms and/or programs, how to properly detect and identify a specific target odor. Inanimate odor detectors can include, for example, products available from Scent Detection Technologies, Ltd. of Herzliya Pituach, Israel, and ScentLogix of Annapolis, Md., including such technologies as ion mobility spectrometry, gas chromatography, mass spectrometry, and liquid chromatography, many or all of which individually or in combination are capable of detecting a target odor(s) at very low concentrations.

Conduit: an apparatus configured to direct or otherwise channel gas from a first location to a second location.

Gas: broadly defined to include pure gases and gas mixtures (including solid and liquid particles entrained therein).

Porous structure: a structure including a plurality of apertures there through for allowing gas to migrate or otherwise be propelled from a first side of the structure to an opposed side of the structure.

Security Screening Session: A period of time during which one or more odor emitters are being screened for a target odor.

Target Odor: an odor of interest that may indicate the presence of a contraband substance such as, for example, illegal narcotics, explosives, chemical weapons, biological weapons, or anything, deemed a potential threat to an area being secured.

Response signal: a specified response given by an inanimate odor detector in response to the inanimate odor detector detecting a target odor.

Triggering event: a situation in which an inanimate odor detector gives a response signal, indicating that a target odor has been detected.

Wall: an object situated in any orientation, having a length much, greater than its thickness, and presenting a substantially continuous surface except apertures or other objects are encountered there through or thereon.

Figure 1:
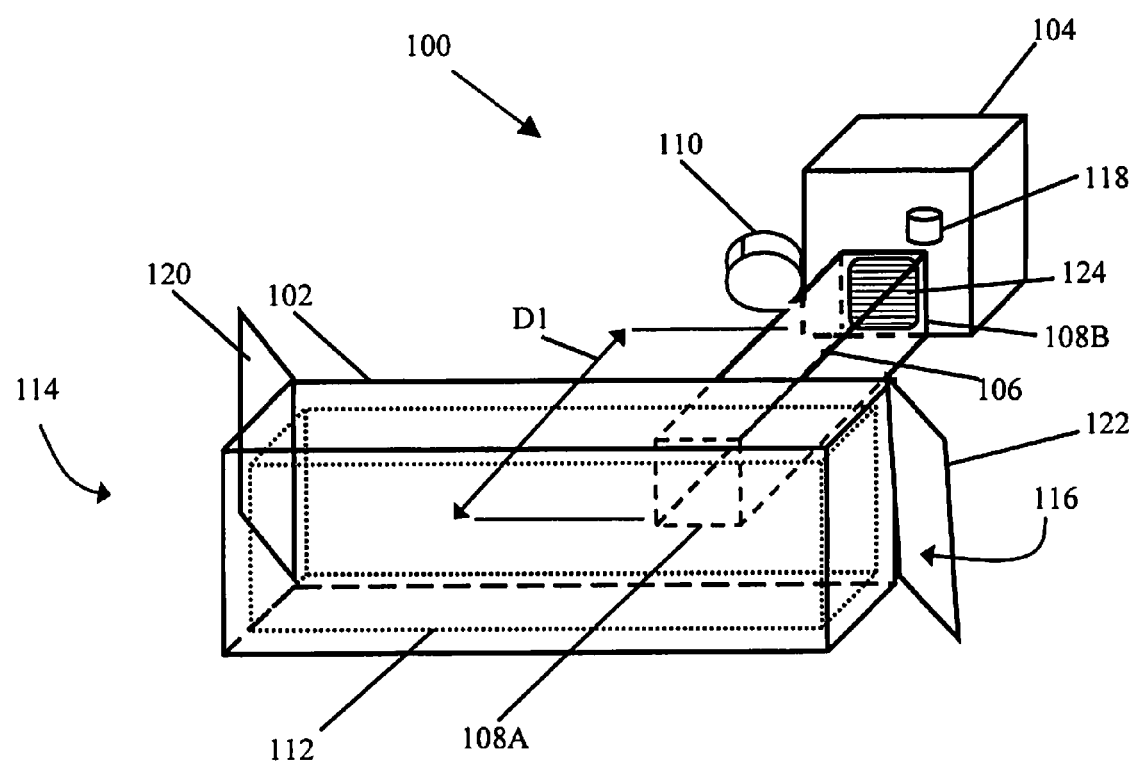
FIG. 1 shows a somewhat schematic perspective view of a target odor detection apparatus.

FIG. 1 shows an embodiment of a security apparatus 100 including a screening station 102, an observation room 104 situated remote from the screening station 102, a conduit 106 including a first end 108A and a second end 108B, and an airflow inducer 110. The screening station 102 includes a three dimensional screening zone 112 where persons, animals, and/or things (collectively, "conveyances" or "odor emitters") pass through in order to be screened for one or more target odors. The screening zone 112 can be configured as a hallway through which multiple persons (up to about 100) can pass at one time at varying rates, of speed and location within the hallway depending on the degree of security desired for the particular situation. The screening zone 112 is defined adjacent an ingress portal 114 through which odor emitters enter the screening station 102, and an egress portal 116 through which odor emitters exit the screening station 102. The observation room 104 can come in many different shapes and sizes depending on the number and type of inanimate odor detector being used (e.g., from about 1 ft$^3$ to a room large enough to house one or more persons. The conduit 106 can be configured to have various possible configurations, but preferably is configured such that the observation room 104 is a distance D1 from about 50 feet to about 250 ft, and most preferably from about 175 ft to about 225 ft, from the screening zone 112. The screening station 102 is attached adjacent the conduit 106 proximate the first end 108A of the conduit 106 and the observation room 104 is attached adjacent the conduit 106 proximate the second end 108B of the conduit. The air inducer 110 is used to push, pull, or otherwise induce gas flow from within the screening zone 112, through the conduit 106 to the observation room 104, taking odors from odor emitters being screened with it so that an inanimate odor detector 118 located in the observation room 104 is exposed to such odors to screen the odors for one or more target odors. The cross-sectional area through which air is flowing preferably ranges from about 1 ft$^2$ to about 10 ft$^2$.

If the inanimate odor detector 118 senses the presence of target odor, it will respond with a response signal to alert an observer and/or a security alarm system that a specific odor has been identified. Security personnel may then direct the interception, detention, or release of the odor emitter or group of odor emitters who emitted the detected target odor. Detaining within the screening station 102 an odor emitter that causes a triggering event may be desirable or undesirable depending on numerous factors including what type of target odor was identified, whether the screening station 102 is fortified or otherwise resistant to explosive blasts and/or small projectiles, and whether the screening station 102 is substantially airtight. For example, if an odor emitter emits a target odor resulting in a triggering event from an inanimate odor detector calibrated for certain high explosives, it may be desirable to lock down the screening station 102 and detain the odor emitter inside if the screening station 102 is reinforced for explosives. If, however, the screening station 102 is not reinforced or otherwise resistant to high explosives, it may be more desirable to temporarily release the odor emitter in a direction away from a protected building or event. If a target odor indicating the presence of narcotics caused a triggering event, however, it may be more desirable to detain the odor emitter regardless of whether the screening station 102 is reinforced because there is no imminent threat of an explosion. Similar logical scenarios are contemplated regarding firearms, chemical weapons, and biological weapons, and the protocol used in these situations would vary based on the embodiment of the security apparatus 100 that is used.

Figure 2A:
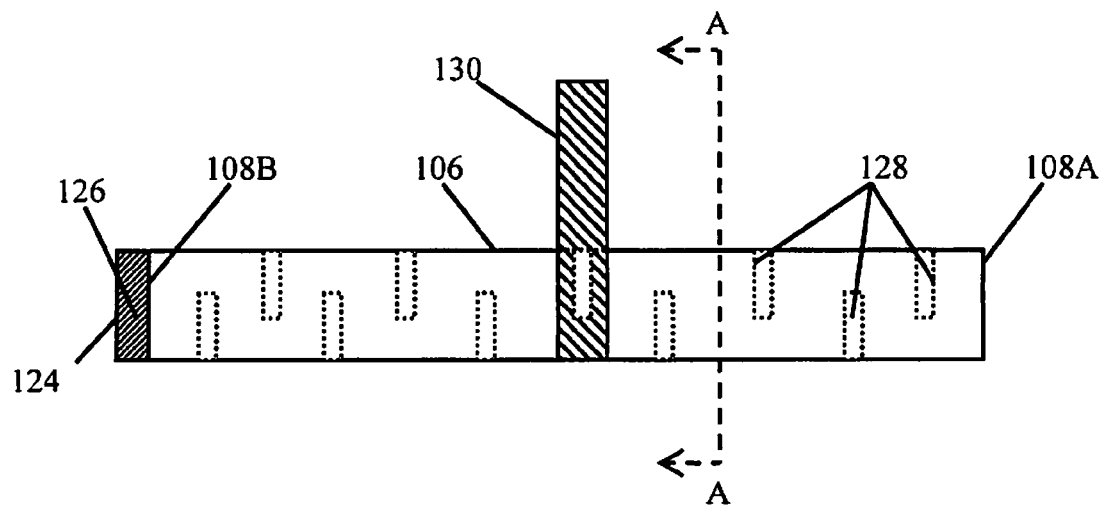
FIG. 2A shows a somewhat schematic side view of a conduit and some security features associated therewith.
Figure 2B:
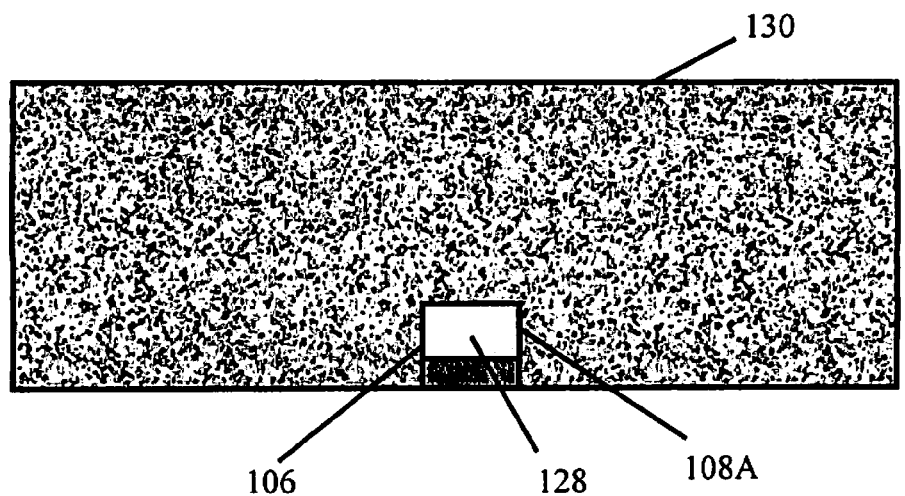
FIG. 2B shows a view cut along line A-A from FIG. 2A.

Preferably, the security apparatus 100 includes a first door 120 for closing the ingress portal 114 and a second door 122 for closing the egress portal 116. Also, the security structure preferably includes a porous structure 124 defining a porous zone 126 between the screening zone 112 and the conduit 106. The porous structure 124 can come in many forms and can be used, for example, to filter air flowing through the porous zone 126, to block an odor emitter from entering the conduit 106, and to act as a visual barrier to prevent an odor emitter from seeing down the conduit. In addition to or in the alternative to use of the porous structure 124, as shown in FIGS. 2A-2B, the conduit 106 can include one or more baffles 128 for protecting the inanimate odor detector 118 and any personnel in the observation room 104 from, for example, explosive debris, small arms fire, chemical weapons use, and/or biological weapons use emanating from or near the screening zone 112. In addition to baffles 128 within the conduit 106, one or more protective walls 130 are included in some embodiments to further isolate the observation room 104 from the screening zone 112.

Figure 3:
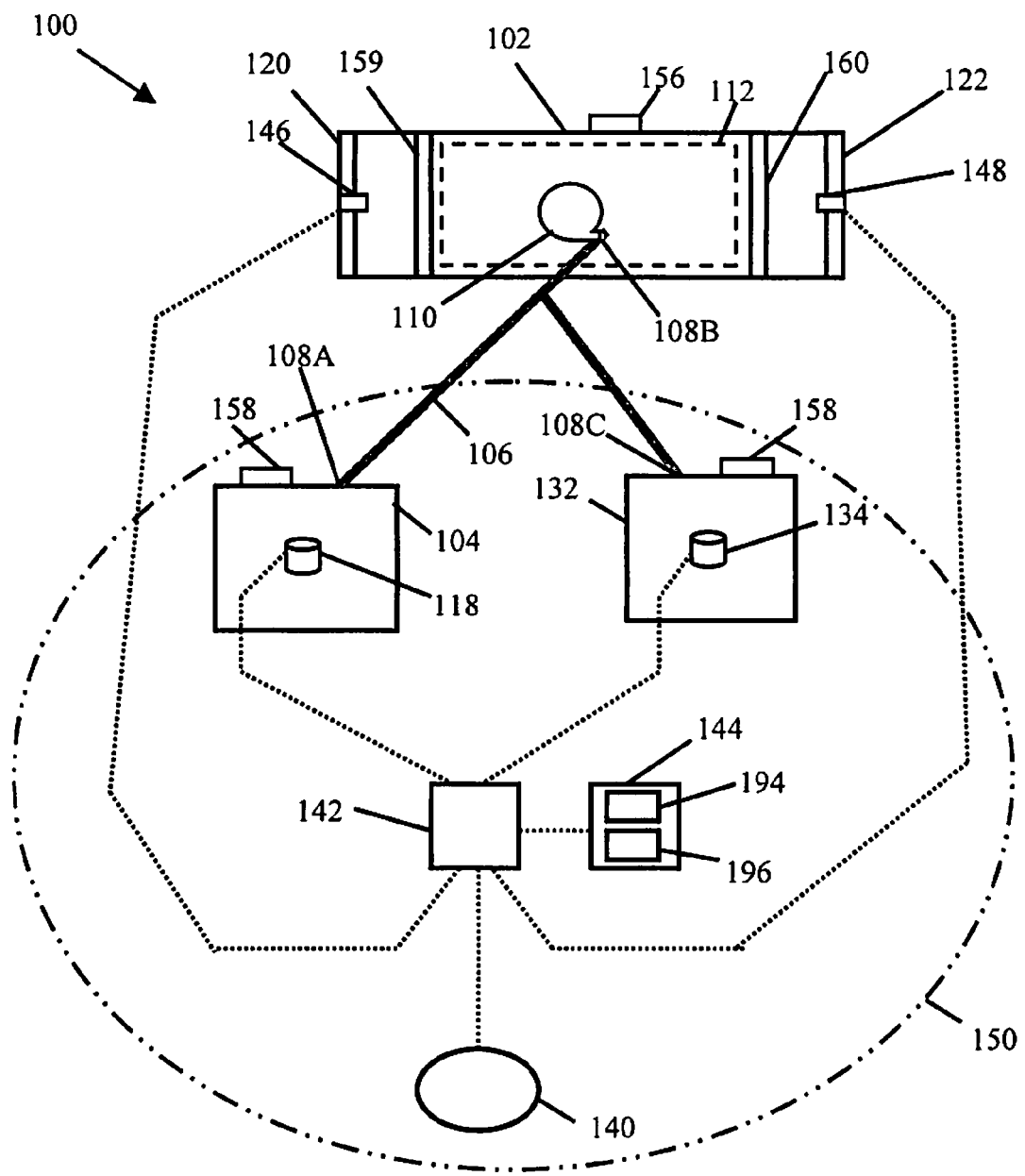
FIG. 3 shows a somewhat schematic side view of a target odor detection apparatus.

In some embodiments as illustrated, for example, in FIG. 3, the security apparatus 100 includes a second observation room 132 remote from the screening zone 112, wherein the conduit 106 further includes a third end 108C attached adjacent the second observation room 132. Preferably, a second inanimate odor detector 134 calibrated to detect one or more target odors is placed in the second observation room 132 to screen odor emitters as they pass through the screening zone. Preferably, the second inanimate odor detector 134 is tasked with screening for a different target odor than the first inanimate odor detector 118 is screening for. Preferably, the inanimate odor detector 134 is in communication with an event indicator 140 and a computational device 142, which further includes an internal or external memory unit 144. The computational device 142 can include, for example, personal computers, laptop computers, integrated circuits (simple or complex such as, for example, an application-specific integrated circuit (ASIC)), embedded computers, servers, control processing units (CPUs), microprocessors. Data corresponding to a minimum threshold of a response signal is saved, uploaded, downloaded, or otherwise provided to the memory unit 144. During operation of the security apparatus 100, the engagement apparatus 136 is substantially continuously monitored by the computational device 142 so that the event indicator 140 is activated if/when an inanimate odor detector gives a response signal within calibration parameters.

Figure 4A:
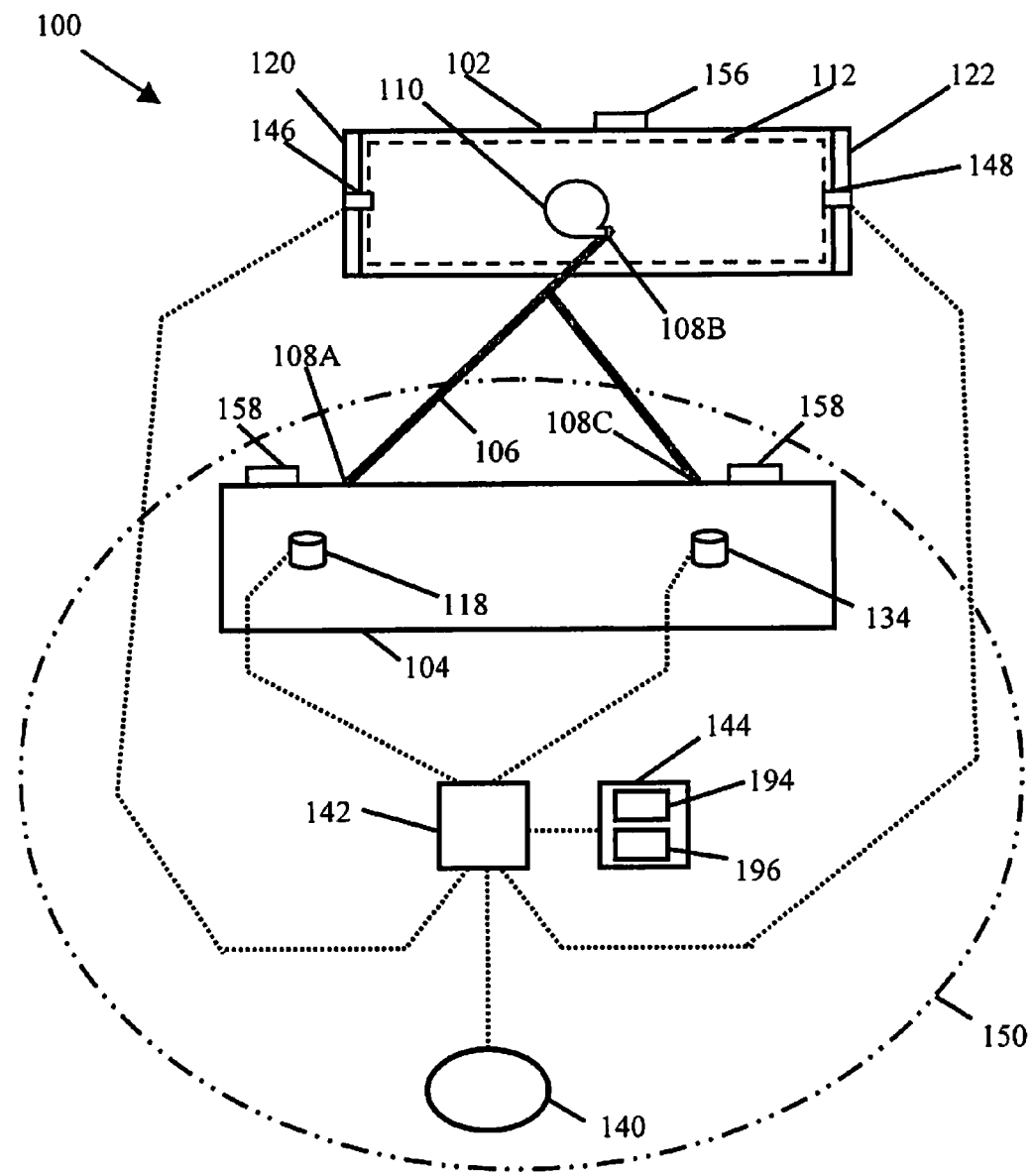
FIG. 4A shows a somewhat schematic side view of a target odor detection apparatus.
Figure 4B:
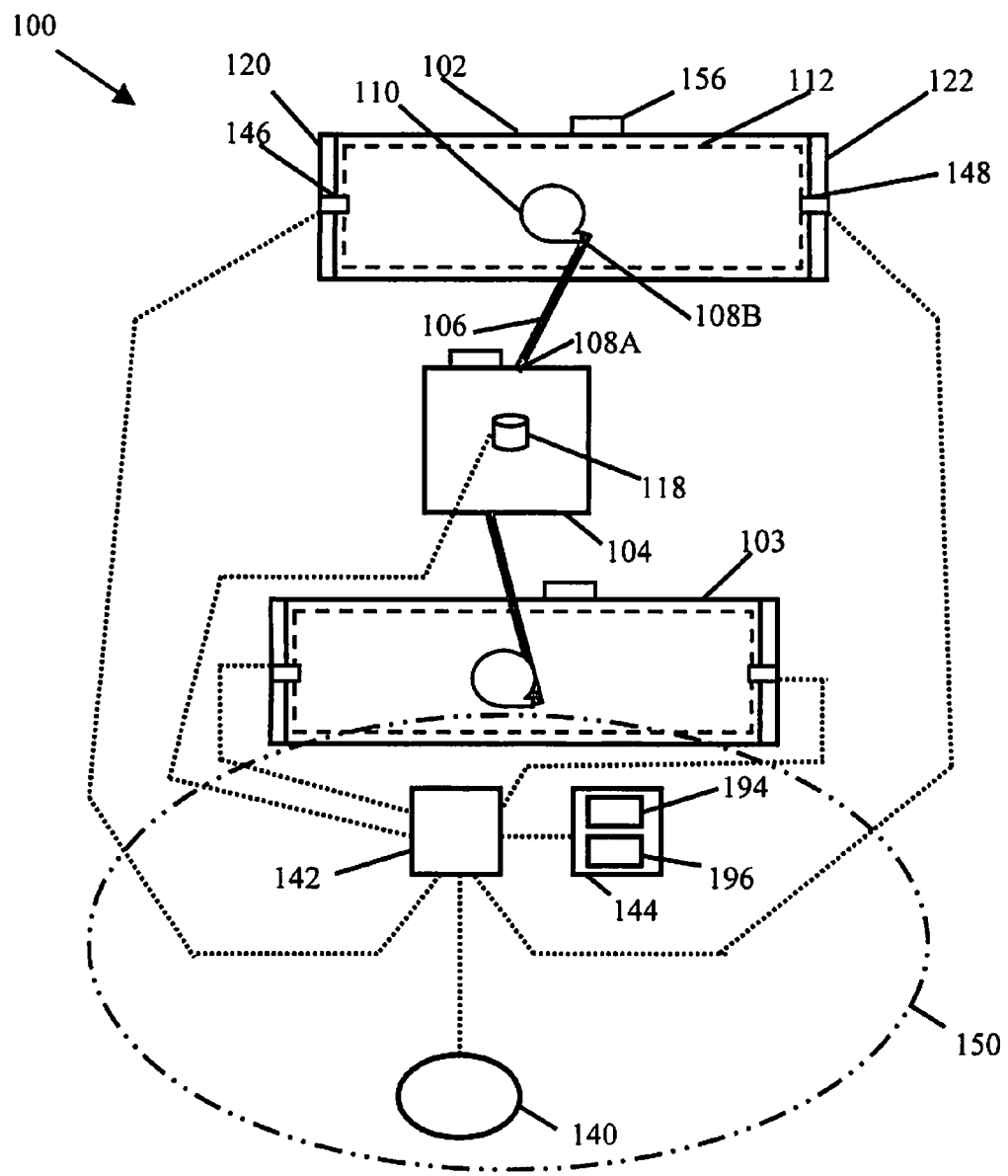
FIG. 4B shows a somewhat schematic side view of the target odor detection apparatus shown in FIG. 4A.

The event indicator 140 can come in many different forms including, for example, a siren, a flashing light, and/or one or more security assets that can be activated in response to a triggering event. In one example, the security apparatus 100 includes a first lock 146 (e.g., an automated and/or manual bolt lock or magnetic lock), a second lock 148, and a control system 150 which can include, for example, the inanimate odor detector 134, the event indicator 140, the computational device 142, and the memory unit 144. The first door 120 is engageable with the first lock 146 and the second door is engageable with the second lock 148, and the lock status of one or all doors is/are preferably monitored and partially or completely controlled by the control system 150. In one embodiment wherein at least two separate inanimate odor detectors are used to screen odor emitters, the resultant control response based on a triggering event initiated by, for example, the first inanimate odor detector 118 is different from the resultant control response based on a triggering event initiated by the second inanimate odor detector 134. As shown in FIG. 4A, the first inanimate odor detector 118 and the second inanimate odor detector 134 can be in the same observation room 104. Regardless of how the inanimate odor detectors are situated, the first inanimate odor detector 118 can be associated with a first type of triggering event (e.g., explosive material), whereas the second inanimate odor detector 134 is associated with a second type of triggering event (e.g., illegal narcotics). The control response to the first triggering event can be, for example, to activate, close, and lock the first door 120 and the second door 122, whereas the control response to the second triggering event can be, for example, to activate, close, and lock only one of the doors, activate a siren and/or flashing light, or do nothing. In a related embodiment shown in FIG. 4B, a single inanimate odor detector 118 can be used to screen a plurality of screening stations including, for example, the screening station 102 shown in FIG. 4A and a second screening station 103.

Preferably, in the various examples described above, air is drawn into the security apparatus 100 through an ingress vent 156 wherein the ingress vent 156 is preferably located adjacent the screening zone 112. Also, preferably, air flows from the screening zone 112, through the conduit 106, into the observation room 104 (and in the second observation room 132, if applicable), and out one or more egress vents 158, one of which is preferably located adjacent the observation room 104.

FIG. 4 also shows a preferred configuration in which a first inner barrier 159 and a second inner barrier 160 are included. These inner barriers can include, for example, actual doors or downward-facing blower fans (commonly referred to as "air curtains"). A purpose of the inner barriers is to further insulate the air within the screening zone 112 from air outside the screening station 102 with regard to, for example, temperature, humidity, and/or odors outside the screening station 102. Also, the space between the second inner barrier 160 and the second door 122 allows time for the second door 122 to become locked during a triggering event before the odor emitter(s) in the screening station 102 have had time to pass through the second door 122.

Figure 5:
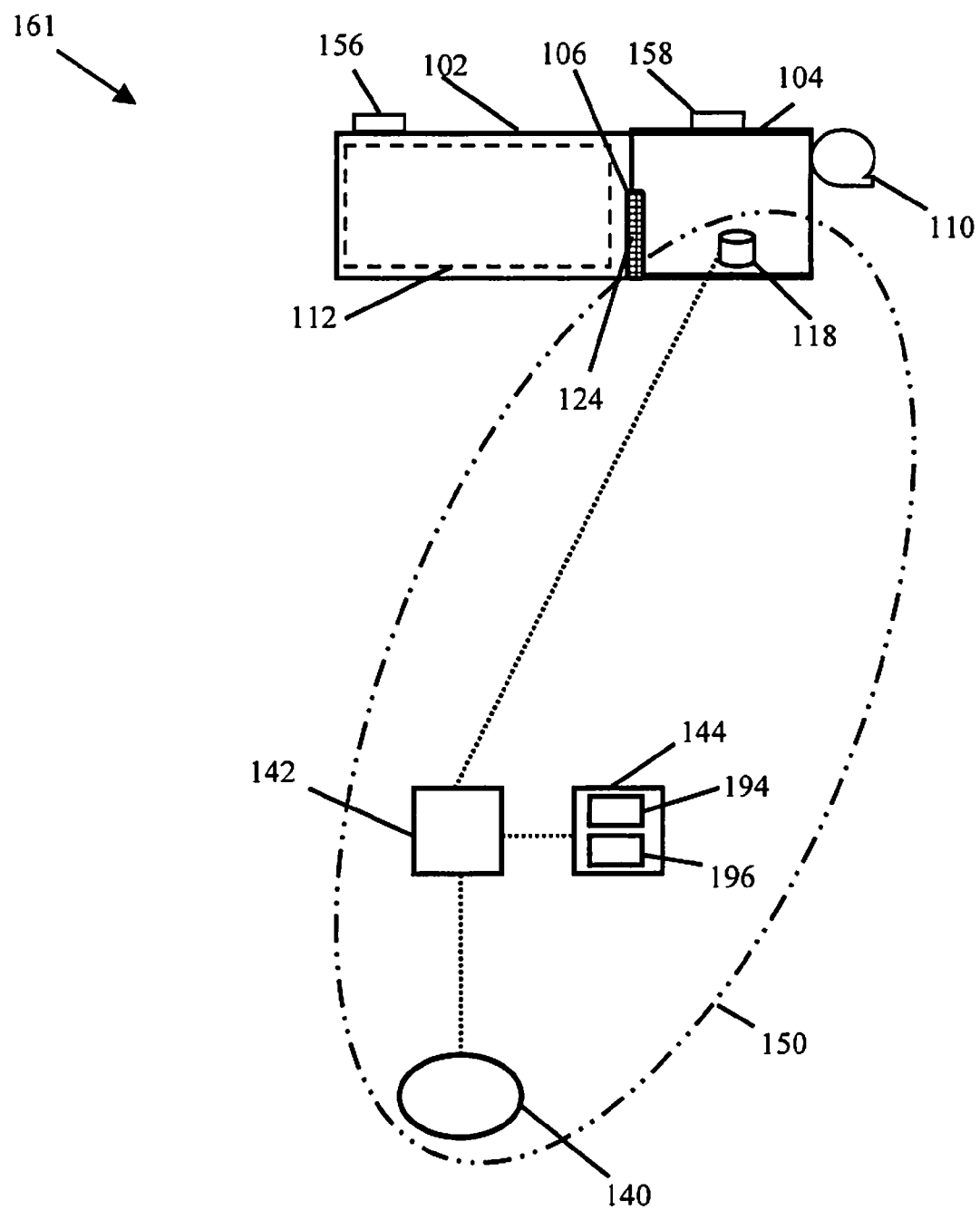
FIG. 5 shows a somewhat schematic end view of a target odor detection apparatus.

FIG. 5 shows an end view of a security apparatus 161 that includes the screening station 102, the observation room 104, the conduit 106, the airflow inducer 110, the screening zone 112, the inanimate odor detector 118, and the porous structure 124; however, the observation room 104 is not situated remote from the screening station 102 and the conduit 106 consists essentially of the porous structure 124.

Figure 6:
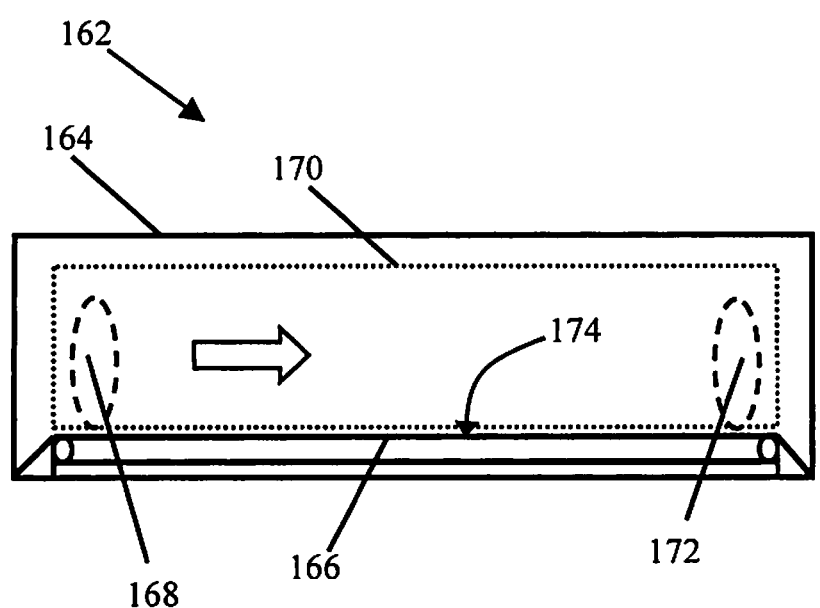
FIG. 6 shows a somewhat schematic side view of a screening station.

FIG. 6 shows part of a security apparatus 162 including a screening station 164 that further includes a conveyor system 166 to convey an odor emitter from a first location 168 within a screening zone 170 to a second location 172 within the screening zone 170. The conveyor system 166 further includes a conveyor support surface 174 for supporting, an odor emitter during a screening period. The duration of the screening period generally depends on the speed of the conveyance system because odor emitters preferably remain stationary relative to the conveyor support surface 174 during the screening period. By providing the conveyance system 166, the movement of multiple odor emitters through the screening zone 170 is standardized to better ensure quality screening results by presenting a similar test sample to the inanimate, odor detector 118 for each odor emitter. The conveyance system 166 can be in the form of, for example, one or more conveyor belts propelled by a motor or an escalator including a plurality of steps.

Figure 7:
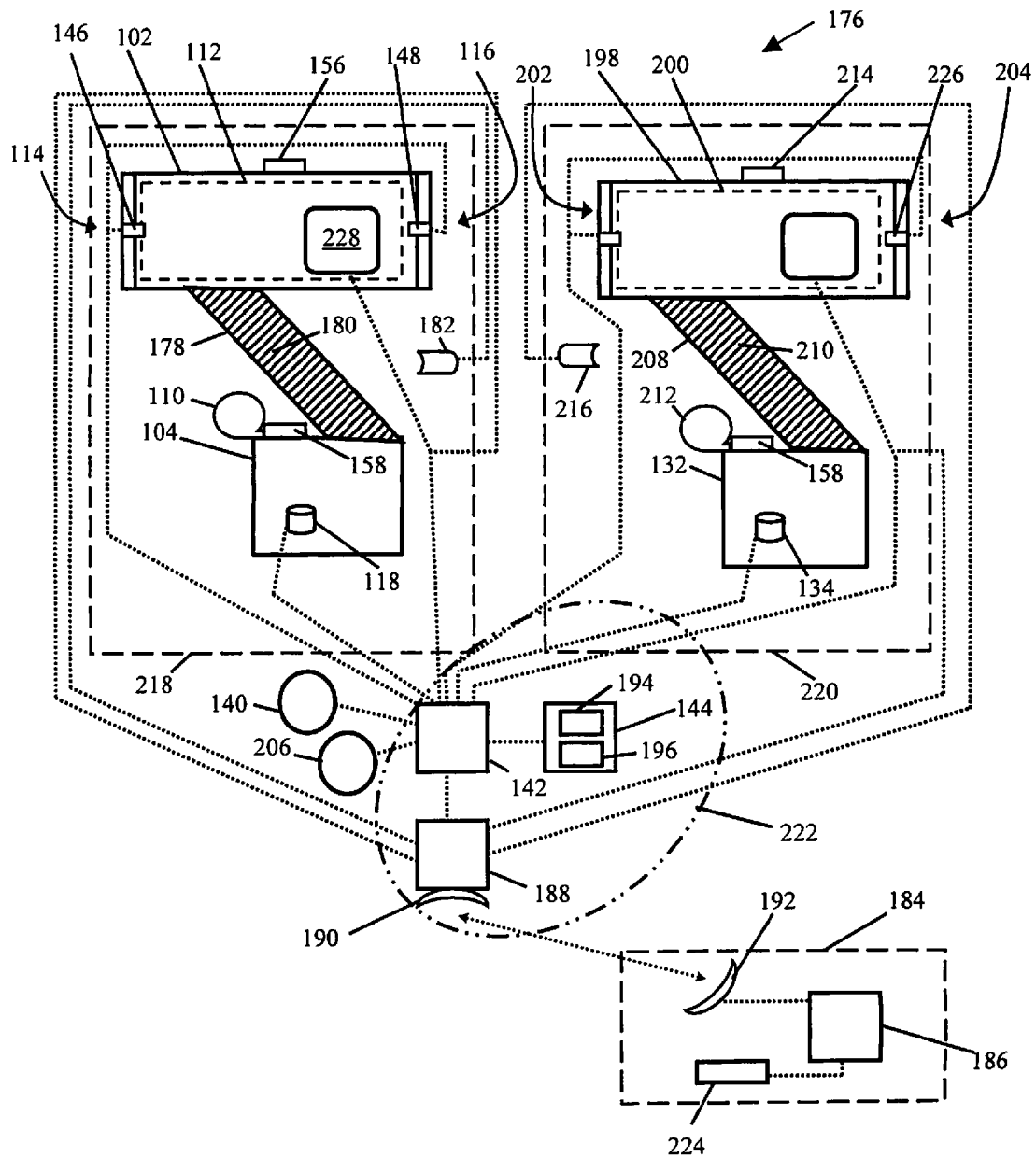
FIG. 7 shows a somewhat schematic side view of a target odor detection apparatus.

FIG. 7 shows a security apparatus 176 including the screening station 102, the observation room 104, the airflow inducer 110, the screening zone 112, the ingress portal 114, the egress portal 116, and the inanimate odor detector 118 located in the observation room 104. The security apparatus 176 further includes a first enclosed passageway 178 defining a first transfer zone 180 between the screening zone 112 and the observation room 104, wherein the first enclosed passageway 178 is attached adjacent the screening station 102 and adjacent the observation room 104 to provide a passageway for gas to flow from the screening zone 112, through the transfer zone 180, to the observation room 104. The security apparatus 176 also includes a first camera 182 for acquiring a first set of visual data from a first area of interest in or adjacent the security apparatus 176. The security apparatus 176 also includes a remote supervision zone 184 including an electronic display apparatus 186 for a person to remotely monitor the first area of interest. A relay system 188 is also preferably provided to relay visual data from the first camera 182 to the electronic display apparatus 186. Preferably, the relay system 188 includes a first visual data transmitter 190 and a first visual data receiver 192.

In one embodiment, visual data (e.g., video or time lapse photography) is recorded in temporary memory storage 194 (e.g., volatile memory such as, for example, random access memory (RAM) of various forms) and such visual data is maintained for a limited period of time (e.g., one week) before it is deleted or otherwise overwritten by more current visual data. If a triggering event occurs, in response to a signal from the sensing device 138, the computational device 142 begins recording visual data on permanent memory storage 196 (e.g., non-volatile memory of various forms including read only memory (ROM) of various forms) and retrieves some or all of the visual data stored on temporary memory storage 194 and saves that visual data to permanent memory 196. Additionally or alternatively, if a triggering event occurs, in response to a response signal, the computational device 142 flags the visual data recorded proximate that time period with a time stamp so that particular portion of recorded video is easily found and/or accessed at a later time.

FIG. 7 also shows a second screening station 198 including a second screening zone 200 defined between a second ingress portal 202 and a second egress portal 204. The second observation room 132 is also shown. The second inanimate odor detector 134 is in communication with a second event indicator 206 and the computational device 142, which further includes the internal or external memory unit 144. Data corresponding to the timing of a response signal is saved, uploaded, downloaded, or otherwise provided to the memory unit 144. During operation of the security apparatus 176, one or more animate odor detectors (e.g., the second animate odor detector 134) are substantially continuously monitored by the computational device 142 so that the second event indicator 206 is activated if/when an inanimate odor detector gives a response signal. A second enclosed passageway 208 defines a second transfer zone 210, wherein the second enclosed passageway 208 is attached adjacent the second screening station 198 and the second observation room 132 to provide a passageway for gas to flow from the second screening zone 200, through the second transfer zone 210, to the second observation room 132. The second inanimate odor detector 134 is located in the second observation room 132, and a second air inducer 212 is provided for inducing air flow from within the second screening zone 200, through the second transfer zone 210, and to the second observation room 132 to entrain odors in the second observation room 132 that were emitted in the second screening zone 200 so that the second inanimate odor detector 134 is exposed to the entrained odors to screen the odors for one or more target odors. A second ingress vent 214 is preferably included to selectively draw ambient air into the screening zone as needed.

Preferably, the security apparatus 176 further includes a second camera 216 for acquiring a second set of visual data from a second area of interest. In one embodiment, the first area of interest is located in a first geographic area 218 including the first screening station 102 and the first observation room 104, and the second area of interest is located in a second geographic area 220 including the second screening station 198 and the second observation room 132. In this embodiment, the relay system 188 relays the second visual data from the second camera 216 to the electronic display apparatus 186, and a person can remotely monitor the first area of interest and the second area of interest at the remote supervision zone 184. The first geographic area 218 can be, for example, at least 50 feet from the second geographic area 220. In other embodiments, the first geographic areas 218 can range from about 1000 ft to about 5500 ft from the second geographic area 220. In other embodiments, the first geographic area 218 is at least 100 miles from the second geographic area 220, and these areas can be separated by thousands of miles if necessary. In other embodiments, the first geographic area 218 is a distance of at least about 5000 feet from the second geographic area 220 and the remote supervision zone 184, and the second geographic area 220 is a distance of at least about 5000 feet from the remote supervision zone 184. These distances are made possible by modern wired and/or wireless communications technologies including, without limitation, cellular communications, satellite communications, Wi-Fi™ or other IEEE 802.11 standard based technology, Bluetooth™ technology, and other electromagnetic communication technologies whether digital or analog.

With regards to the security apparatus 176 described above, the first enclosed passageway 178 and the second enclosed passageway 208 can be elongate conduits, providing for increased distance between the respective screening stations and observation rooms. Alternatively or additionally, the first enclosed passageway 178 and the second enclosed passageway 208 can include, for example, porous structures like the porous structure 124 defined above with regards to the security apparatus 100 in FIG. 5.

The security apparatus 176 can further include a control system 222 in communication with the first inanimate odor detector 118 and a manual input apparatus 224 located in the remote supervision zone 184. The manual input apparatus 224 is for selective activation by a person in response to observing an event of interest displayed on the electronic display apparatus 186, whereby activation of the manual input apparatus 224 and/or triggering of a response signal causes the control system 222 to generate a control signal directed to a security asset 226 to activate the security asset 226. In embodiments including the second inanimate odor detector 134, the control system 222 is in communication with the second inanimate odor detector 134 and the manual input apparatus 224. A security asset 226 can include, for example, a door, a door lock, an air inducer, a siren, a light, a fire suppression system (e.g., sprinkler system), a repulsing agent emitter (e.g., pepper spray nozzle), and/or a specially trained person contacted via telecommunication equipment (e.g., a text message or an e-mail message indicating an event of interest has occurred at a specified location).

In related embodiments, the security apparatuses 176 described above can further include an electronic scanning apparatus 228 located within or adjacent the screening station 102. By including the scanning apparatus 228, an odor emitter passing through the screening zone 112 can be screened by the inanimate odor detector 118 for target odors and also screened by a person monitoring the electronic scanning apparatus 228. The electronic scanning apparatus 228 can include, for example, a metal detector and/or a body image scanner as used in many airports. In a preferred embodiment, the electronic scanning apparatus 228 is in communication with the relay system 188 and/or the control system 222 so that events that trigger the electronic scanning apparatus 228 observed by a person in the remote supervision zone 184 or otherwise made to generate a control signal directed to one or more security assets 226 to activate the security asset 226.

Figure 8A:
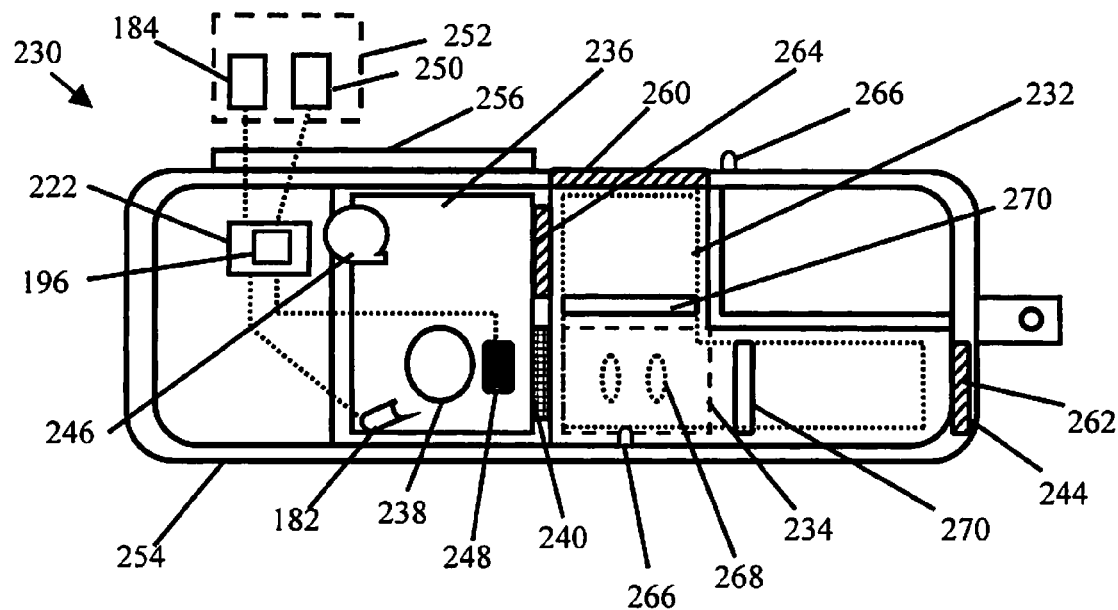
FIG. 8A shows a somewhat schematic top view of a mobile target odor detection apparatus.
Figure 8B:
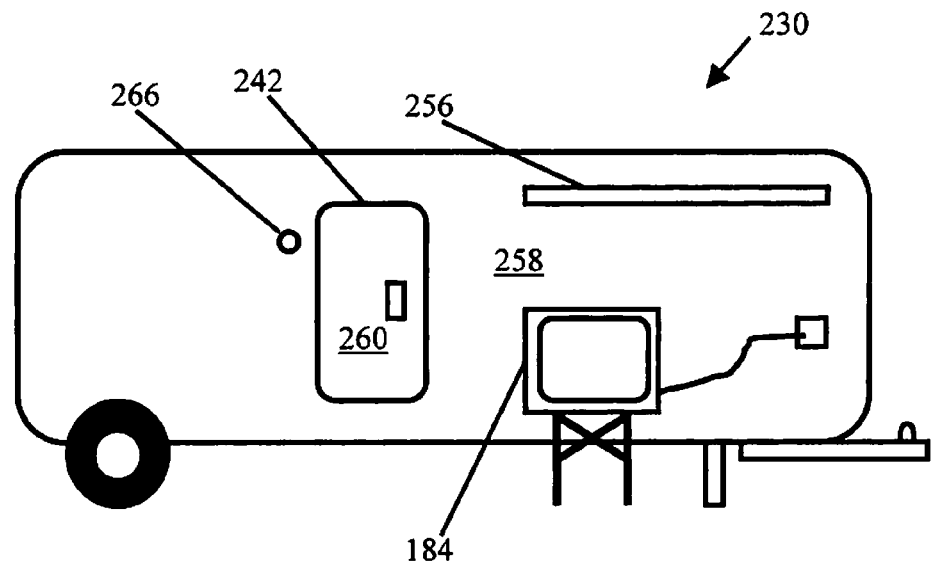
FIG. 8B shows a somewhat schematic side view of the mobile target odor detection apparatus shown in FIG. 8A.

FIGS. 8A and 8B show a mobile version of a security apparatus 230 including a screening chamber 232; a screening zone 234 within the screening chamber 232; an observation chamber 236 for situating an inanimate odor detector 238 to screen odor emitters for target odors as the odor emitters pass through the screening zone 234; a porous structure 240 through which air can flow from the screening zone 234 to the observation chamber 236; at least one ingress portal 242 through which an odor emitter can enter into the screening chamber 232; preferably, an egress portal 244 through which an odor emitter exits from the security apparatus 230; an air flow inducer 246 for inducing air flow from within the screening zone 234, through the porous structure 240, and into the observation chamber 236 to be screened by the inanimate odor detector 238 calibrated to detect a target odor and generate a response signal when detecting a target odor; and an inanimate odor detector 238 in communication with an event indicator 250. The inanimate odor detector 238 is calibrated and/or programmed to generate a response signal if the inanimate odor detector 238 senses a target odor, the generation and submission of which, in turn, triggers the event indicator 250 to indicate that a target odor has been detected. Other features described above regarding other non-mobile embodiments of security devices can be incorporated into the mobile security apparatus 230 such as, for example, the control system 222 shown in FIG. 7. The mobile security apparatus 230 is preferably housed within a trailer, but other embodiments are contemplated such as, for example, a bus, an RV, a van or other similarly sized mobile vehicle.

Preferably, the mobile security apparatus 230 also includes a supervision zone 252 (which optionally can be remote from the screening chamber 232 as described with respect to other embodiments above), a first camera 182, and an electronic display apparatus 184. If the supervision zone 252 is located directly outside a vehicle structure 254, a retractable awning 256 is preferably attached adjacent an outside surface 258 of the vehicle structure 254 to provide some protection from the elements. Preferably, a first door 260 is included to cover the ingress portal 242 and, if applicable, a second door 262 is preferably provided to cover the egress portal 242. In embodiments in which access to the observation chamber 236 is made through the ingress portal, an access door 264 is preferably provided to separate the screening chamber 232 from the observation chamber 236. In one embodiment, the security apparatus 230 includes one or more queue indicators 266 such as, for example, lights that shine green when it is time for an odor emitter to advance and that shine red when it is time for an odor emitter to stand still. Additionally or alternatively, one or more queue indicators may include an automated voice system that gives audible commands through a speaker system, wherein different commands in different languages can be stored in a memory module such as, for example, permanent memory storage 196. These and related features are also used in other non-mobile embodiments described herein and, preferably, the violation of a queue indicator results in a triggering event.

In one embodiment, a pair of foot pads 268 (e.g., foot shaped decals) can be provided to show an odor emitter how and where to stand in the screening zone 234. To better ensure that an odor emitter is standing in the proper position, the foot pads 268 may further include one or more sensors (e.g., a piezoelectric pressure pad, an accelerometer, or other sensor like those used with respect to the engagement apparatuses described herein) to detect whether an odor emitter is stepping on the foot pads 268 properly. These and related features are also used in other non-mobile embodiments described herein and, in some embodiments, detection of an improper stance results in, for example, a local alarm to notify local security personnel to assist an odor emitter through the applicable screening zone. Alternatively, intentional improper standing as evidenced, for example, by camera footage, can result in an automatic or manual triggering event.

In some embodiments, the screening zone 234 is further isolated by barriers 270 (e.g., flexible polymeric curtains or small doors) to further reduce the volume of air in the screening zone 234.

Figure 9:
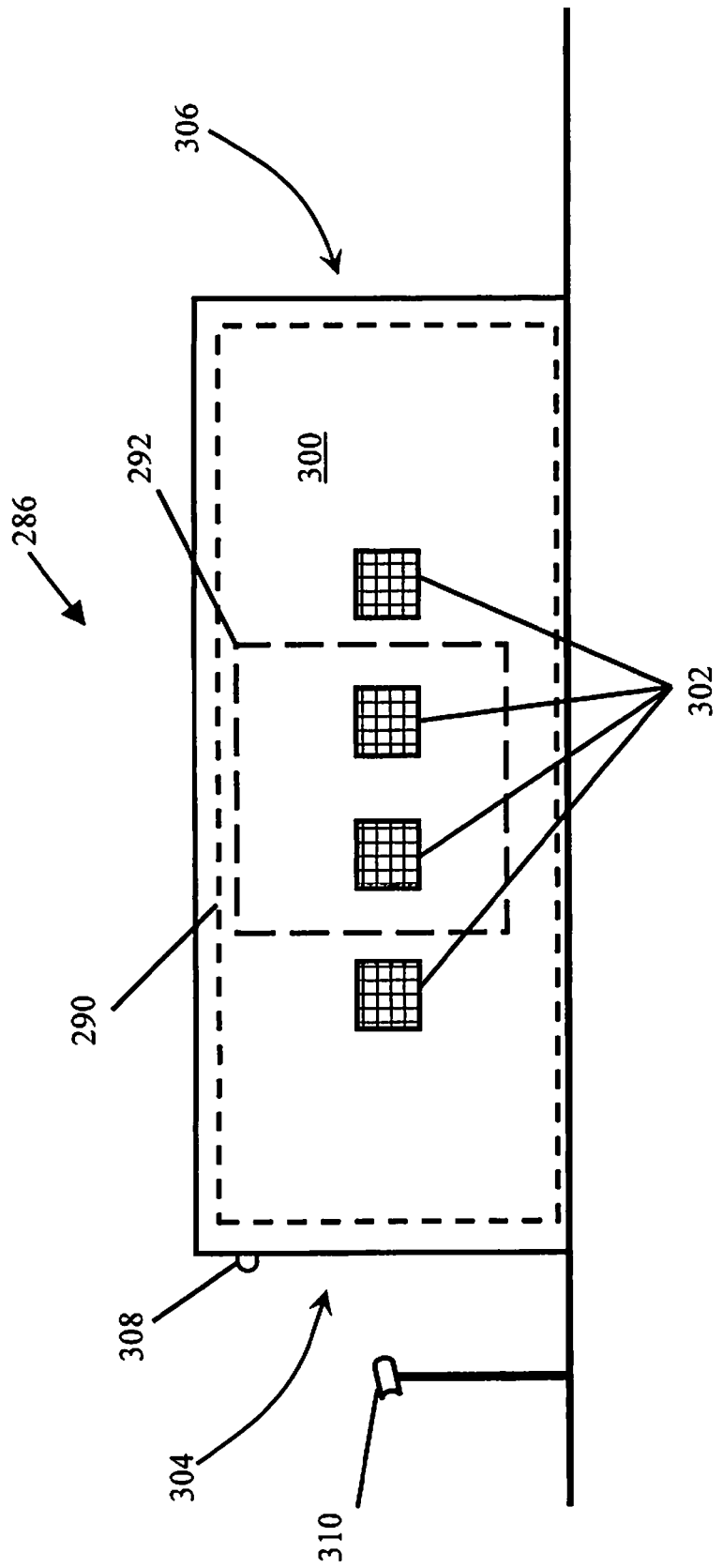
FIG. 9 shows a somewhat schematic side view of a target odor detection apparatus.
Figure 10:
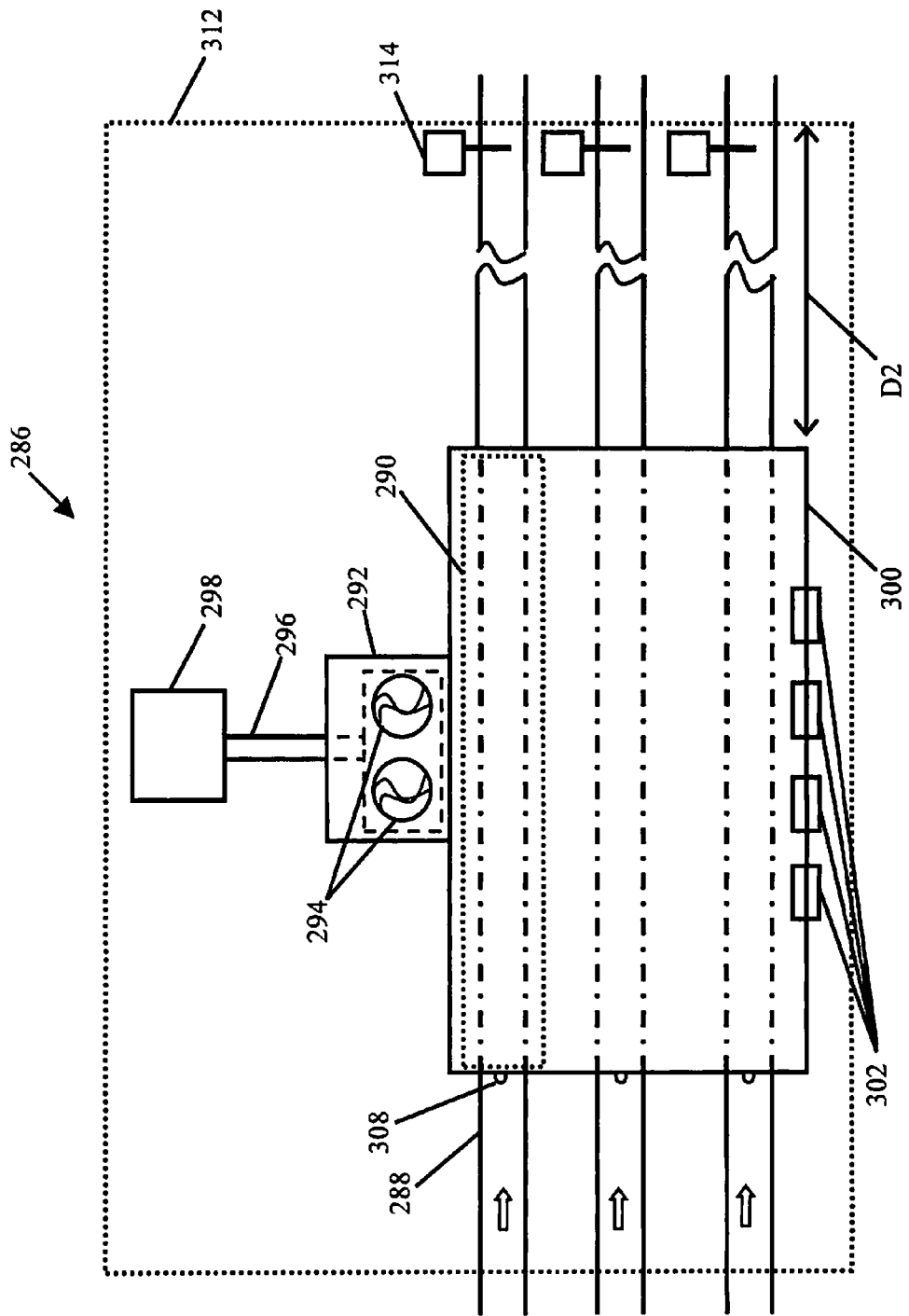
FIG. 10 shows a somewhat schematic top view of the target odor detection apparatus shown in FIG. 9.

FIGS. 9 and 10 show a security apparatus 286 for screening multiple conveyances (e.g., cars, trucks, tractors, motorcycles). The security apparatus 286 includes at least one lane 288 for a conveyance to pass over, a substantially enclosed passageway 290 through which the at least one lane 288 extends, a primary exhaust chamber 292, an air mixer 294 (e.g., mechanical fan) for creating turbulent air conditions within the primary exhaust chamber 292, a duct 296 for directing a fraction of the total airflow in the primary exhaust chamber 292 to an observation room 298 similar or identical to the observation rooms (104, 132) described above with respect FIGS. 1, 3, and 7. The fraction of total airflow directed through the duct 296 preferably ranges from about 5% to about 15%, and more preferably about 10%, by volume of the total airflow flowing through the primary exhaust chamber 292. The passageway 290 further includes a lateral portion 300 including a plurality of air inducers 302 for directing air within the passageway 290 to the primary exhaust chamber 292; an entrance aperture 304 through which conveyances can enter the passageway 290; and an exit aperture 306 through which conveyances can exit the passageway 290.

Preferably, the flow of traffic along each lane is controlled by one or more queue indicators 308 (e.g., a traffic light). Preferably, a maximum speed limit for conveyances is posted and monitored for each conveyance as each conveyance passes through the passageway 290. Such speeds are preferably monitored using, for example, radar or laser detection devices 310 commonly used by traffic law enforcement personnel. A security zone 312 is defined and controlled up to a defined distance D2 from the exit aperture 306 so that if an inanimate odor detector in the observation room 298 generates a response signal, security personnel and/or automated control system(s) have adequate time to stop traffic within the security zone 312 to more closely inspect the one or more conveyances that were passing through the passageway 290 near the time when the inanimate odor detector exhibited a response signal. This can be accomplished at least in part, for example, by one or more security barriers 314. The defined distance D2 preferably ranges from about one quarter mile to about one mile and, more preferably, from about one half mile to about three-quarters of a mile.

By creating turbulent air conditions in the primary exhaust chamber 292, the air therein quickly becomes well-mixed such that a sample of the air within the primary exhaust chamber 292 is a more reliable cross-sectional sample of the entire air environment within the passageway 290. Thus, when air from the duct 296 is exposed to an inanimate odor detector, the inanimate odor detector is more likely to detect any target odor that may be (or very recently was) present within the covered passageway 290.

Various embodiments disclosed herein can be used in many different security situations and applications including, for example, airport security, building security, event security (e.g., a large outdoor concert, a collegiate or professional sporting event), and government structure security.

One object of the disclosure is to provide an apparatus to provide distance between the screening zone where odor emitters pass through and the observation room where a screening inanimate odor detector is usually present, potentially with accompanying personnel. Placing an observation room a minimum distance from a screening zone is important for various reasons including protecting an inanimate odor detector from weapons used in or near the screening zone (e.g., explosives, chemical weapons, and biological weapons); and decreasing the chance that human or animal odor emitters will be aware that the screening inanimate odor detector is screening them.

Yet another object of the disclosure is to provide a security apparatus that can isolate, repulse, or otherwise control an odor emitter that causes a triggering event. If a non-threatening target odor is detected (e.g., illegal narcotics), the suspected odor emitter can be enclosed within a screening station. Alternatively, if a threatening target odor is detected (e.g., high explosives), the suspected odor emitter can be repulsed from the screening station away from the building/event being secured by use of a repulsing agent (e.g., an automated pepper spray nozzle within the screening station). If the screening station is blast resistant, it may be better to isolate an odor emitter suspected of carrying high explosives within the screening station by automatically closing and locking any applicable doors. If a chemical weapon or biological weapon is detected, an embodiment of a security apparatus as described herein can be configured to automatically close all vents, doors, and other openings to the screening station, thereby virtually sealing the screening station so that such weapons cannot be spread outside of the screening station. Various control logic options using the security apparatuses described herein and variations thereof are contemplated in which certain types of triggering events cause certain security assets to be activated in a specified order or manner. The resultant security measures taken in any given scenario will ultimately depend on the programming of the applicable controller (and associated software, firmware, and/or otherwise), the specific configuration and construction of the security apparatus being used, and the number and types of target odors being screened at any one time.

Another object of the disclosure is to provide a highly reliable security apparatus for screening one or more target odors while also screening odor emitters using other technologies including metal detection, body scanning, bio-scanning (e.g., finger-print scans, retinal scans), badge scanners, and other types of security scanning and screening devices.

The previously described embodiments of the present disclosure have many advantages, including consistency in sensing target odors, protection for screening inanimate odor detectors and odor emitters alike, protection from blasts or flying projectiles, screening for different types of target odors at one time, visual monitoring of multiple screening stations located very far apart from one another and far apart from the remote supervision zone, automated sensor monitoring of multiple screening stations located very far apart from one another and far apart, mobility of certain versions of the security apparatus, flexibility in programming a security apparatus controller based on the particular situation/event/building for which a security apparatus will be used to protect, and other advantages described herein.

The ability to rapidly scan conveyances moving at high rates of speed is a significant improvement over scanning conveyances (e.g., cars) one by one at checkpoints where to conveyances must each stop in single file fashion for sometimes extended periods of time. Although the rapid screening techniques described herein with respect to moving conveyances is not necessarily reliable at detecting small quantities (i.e., less than about 10 kilograms) of a contraband substance (e.g., explosives), the objective is to rapidly eliminate someone to move a conveyance proximate to a secured area and, for example, detonate a large amount of explosives. Similarly, detection of small stashes of narcotics crossing over a federal border is not the goal for this specific exemplary technology. Rather, a primary goal is to rapidly and efficiently identify large quantities of narcotics and other illegal substances to disrupt significant shipments of illegal contraband. Thus, for this particular application, detection of small quantities is not nearly as important as detecting large quantities of contraband substances.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

Any element in a claim that does not explicitly state "means for" performing a specified function, or "step for" performing a specific function, is not to be interpreted as a "means" or "step" clause as specified in 35 U.S.C. §112, ¶ 6. In particular, the use of "step of" in the claims herein is not intended to invoke the provisions of 35 U.S.C. §112, ¶ 6.

What is claimed is:

1. A security apparatus comprising:
a screening station including a screening zone defined between an ingress portal and an egress portal of the screening station for an odor emitter to pass through the screening zone;
a remote observation room;
a conduit including a first end and a second end, the conduit attached adjacent the screening station proximate the first end and attached adjacent the observation room proximate the second end, wherein gas can flow freely through the conduit from the screening station screening zone to the observation room;
an inanimate odor detector located in the observation room and configured to identify at least one target odor;
an airflow inducer for inducing airflow from within the screening zone, through the conduit, and to the observation room to entrain odors in the observation room that were emitted in the screening zone so that the inanimate odor detector is exposed to the entrained odors to screen the odors for one or more target odors.

2. The security apparatus of claim 1 further comprising a porous structure defining a porous zone between the screening zone and the conduit, whereby air flows from within the screening zone, through the porous zone, through the conduit, and to the observation room to entrain odors in the observation room that were emitted in the screening zone so that the inanimate odor detector is exposed the entrained odors to screen the odors for one or more target odors.

3. The security apparatus of claim 1 further comprising a conduit configuration wherein the observation room is from about 50 feet to about 250 feet from the screening zone.

4. The security apparatus of claim 1 further comprising a conduit configuration wherein the observation room is at least about 200 feet from the screening zone.

5. The security apparatus of claim 1 further comprising:
a second remote observation room;
the conduit including a third end, the conduit attached adjacent the second observation room proximal the third end, wherein gas can flow freely through the conduit from the screening station screening zone to the second observation room;
a second inanimate odor detector located in the second observation room and configured to identify at least one target odor that is different from the target odor the first inanimate odor detector is screening for;
the airflow inducer for inducing airflow from within the screening zone, through the conduit, and to the second observation room to entrain odors in the second observation room that were emitted in the screening zone so that the second inanimate odor detector is exposed to the entrained odors for screening the odors for one or more target odors.

6. The security apparatus of claim 5 further comprising:
a first door for closing the ingress portal and a second door for closing the egress portal;
a lock system including a first lock for locking the first door and a second lock for locking the second door;
a control system in communication with the inanimate odor detector and the lock system for controlling the lock status of the first door and the second door based at least in part on information sent from the sensing device to the control system wherein the control system is programmed such that a triggering event initiated by the first inanimate odor detector will result in a first control response and a triggering event initiated by the second inanimate odor detector will result in a second control response, wherein the first control response is different from the second control response.

7. The security apparatus of claim 3 wherein air is drawn into the security apparatus through an ingress vent adjacent the screening zone, and air flows from the screening zone through the conduit, into the observation room, and out of the security apparatus through an egress vent located adjacent the observation room.

8. A security apparatus comprising:
a screening station including a screening zone defined between an ingress portal and an egress portal of the screening station for an odor emitter to pass through the screening zone;
an observation room;
an enclosed passageway defining a transfer zone between the screening zone and the observation room;
an inanimate odor detector located in the observation room; and an airflow inducer for inducing airflow from within the screening zone, through the transfer zone, and to the observation room to entrain odors in the observation room that were emitted in the screening zone so that the inanimate odor detector is exposed to the entrained odors to screen the odors for one or more target odors, wherein the inanimate odor detector is in communication with an event indicator.

9. The security apparatus of claim 8 further comprising:
a second screening station including a second screening zone defined between a second ingress portal and a second egress portal of the second screening station for an odor emitter to pass through the second screening zone; and
a second enclosed passageway defining a second transfer zone between the second screening zone and the observation room.

10. The security apparatus of claim 8 further comprising a conveyance system including a conveyor support surface for an odor emitter to remain still during a screening period, wherein the conveyance system moves the odor emitter at a desired rate from a first location within the screening zone to a second location within the screening zone.

11. The security apparatus of claim 8 further comprising:
a first door for closing the ingress portal and a second door for closing the egress portal;
a lock system including a first lock for locking the first door and a second lock for locking the second door;
a control system in communication with the inanimate odor detector and the lock system for controlling the lock status of the first door and the second door based at least in part on information sent from the inanimate odor detector to the control system.

12. The security apparatus of claim 8 further comprising:
a first camera for acquiring a first set of visual data from a first area of interest in or adjacent the security apparatus;
a remote supervision zone including an electronic display apparatus for a person to remotely monitor the first area of interest;
a relay system for relaying visual data from the first camera to the electronic so display apparatus.

13. The security apparatus of claim 12 comprising the relay system which further comprises a first visual data transmitter and a first visual data receiver.

14. The security apparatus of claim 12 further comprising:
a second screening station including a second screening zone defined between a second ingress portal and a second egress portal of the second screening station for an odor emitter to pass through the second screening zone;
a second enclosed passageway defining a second transfer zone between the second screening zone and the second observation room;
a second inanimate odor detector located in the second observation room;
a second airflow inducer for inducing airflow from within the second screening zone, through the second transfer zone, and to the second observation room to entrain odors in the second observation room that were emitted in the second screening zone so that the second inanimate odor detector is exposed the entrained odors to screen the odors for one or more target odors;
the first camera for acquiring the first set of visual data from the first area of interest, wherein the first area of interest is located in a first geographic area comprising the first screening station and the first observation room;
a second camera for acquiring a second set of visual data from a second area of interest, wherein the second area of interest is located in a second geographic area too comprising the second screening station and the second remote observation room;
the remote supervision zone including the electronic display apparatus for a person to remotely monitor the first area of interest and the second area of interest;
the relay system for relaying the first visual data from the first camera and the second visual data from the second camera to the electronic display apparatus,
wherein the first geographic area is a distance of at least 50 feet from the second geographic area.

15. The security apparatus of claim 11 comprising the enclosed passageway which further comprises an apparatus selected from the group consisting of:
a conduit including a first end and a second end, the conduit attached adjacent the screening station proximal the first end and attached adjacent the observation room proximal the second end, wherein gas can flow freely through the conduit from the screening station screening zone to the observation room; and
a porous structure defining a porous zone between the screening zone and the observation room, whereby air flows from within the screening zone, through the porous zone, and to the observation room to entrain odors in the observation room that were emitted in the screening zone so that the inanimate odor detector is exposed the entrained odors to screen the odors for one or more target odors.

16. The security apparatus of claim 12 comprising:
the remote supervision zone further comprising a manual input apparatus for selective activation by a person in response to observing an event of interest displayed on the electronic display apparatus, whereby activation of the manual input apparatus and/or triggering of the inanimate odor detector causes the control system to generate a control signal directed to a security asset to activate the security asset;
a control system in communication with the inanimate odor detector and the manual input apparatus.

17. The security apparatus of claim 14 comprising:
the remote supervision zone further comprising a manual input apparatus;
a control system in communication with the inanimate odor detector, the second inanimate odor detector, and the manual control apparatus, the manual input apparatus for selective activation by a person in response to observing an event of interest displayed on the electronic display apparatus, whereby activation of the manual input apparatus, triggering of the inanimate odor detector, and/or triggering of the second inanimate odor detector causes the control system to generate a control signal directed to a security asset to activate the security asset.

18. A mobile security apparatus comprising:
a vehicle comprising
a screening chamber including a screening zone defined therein, the screening chamber including a portal through which an odor emitter can enter to be screened for one or more target odors;
an observation chamber;
an enclosed passageway defining a transfer zone between the screening zone and the observation chamber;

an inanimate odor detector located in the observation chamber and configured to identify at least one target odor; and an airflow inducer for inducing airflow from within the screening zone, through the transfer zone, and to the observation chamber to entrain odors in the observation chamber that were emitted in the screening zone so that the inanimate odor detector is exposed to the entrained odors to screen the odors for one or more target odors, an engagement apparatus including a sensing device attached adjacent thereto, wherein the sensing device is in communication with an event indicator, and wherein the inanimate odor detector is in communication with the event indicator to indicate that a target odor has been detected.

19. A security apparatus for screening a conveyance while the conveyance remains in motion, the apparatus comprising:

a structure including a lateral section, the structure defining a passageway through which a conveyance can pass from an entrance aperture to an exit aperture;

a primary exhaust chamber;

a plurality of air inducers attached adjacent the lateral section, wherein the air inducers, when operational, direct air within the passageway to the primary exhaust chamber;

an air mixing apparatus for ensuring turbulent air conditions during operation within the primary exhaust chamber;

a duct attached adjacent the primary exhaust chamber wherein, during operation, a portion of the air flowing through the primary exhaust chamber exits through the duct; and an observation room attached adjacent the duct for receiving air from the passageway and for temporarily housing an inanimate odor detector for screening the air passing through the observation room for a target odor.

20. The security apparatus of claim 19 further comprising:

a security zone extending a distance D from the exit aperture of the structure; and a security barrier within the security zone for prohibiting a conveyance from exiting the security zone if a target odor is detected by an inanimate odor detector during the period of time when the conveyance was in the passageway or between the passageway and the security barrier.

* * * * *